United States Patent [19]

Forman

[11] Patent Number: 5,776,100
[45] Date of Patent: Jul. 7, 1998

[54] NICKEL TITANIUM GUIDE WIRES FOR OCCLUSION AND DRUG DELIVERY

[75] Inventor: Michael R. Forman, St. Paul, Minn.

[73] Assignee: Interventional Innovations Corporation, St. Paul, Minn.

[21] Appl. No.: 719,999

[22] Filed: Sep. 25, 1996

Related U.S. Application Data

[60] Provisional application No. 60/004,349, Sep. 27, 1995.

[51] Int. Cl.$^6$ ................................................ A61M 29/00
[52] U.S. Cl. .................... 604/102; 604/96; 604/281; 606/194
[58] Field of Search ................ 604/96, 280, 281, 604/264, 252, 102; 606/192, 194; 128/772, 657

[56] References Cited

U.S. PATENT DOCUMENTS

| | | | |
|---|---|---|---|
| 4,846,186 | 7/1989 | Box et al. | 128/657 |
| 5,120,308 | 6/1992 | Hess. | |
| 5,174,302 | 12/1992 | Palmer | 128/772 |
| 5,322,508 | 6/1994 | Viera. | |
| 5,345,945 | 9/1994 | Hodgson et al. | 128/772 |
| 5,353,808 | 10/1994 | Viera | 128/772 |
| 5,372,587 | 12/1994 | Hammerslag et al. | |
| 5,397,305 | 3/1995 | Kawula et al. | 604/96 |
| 5,460,187 | 10/1995 | Daigle et al. | 128/772 |
| 5,488,959 | 2/1996 | Ales | 128/772 |
| 5,505,699 | 4/1996 | Forman et al. | 604/96 |
| 5,514,128 | 5/1996 | Hillsman et al. | 606/7 |
| 5,558,643 | 9/1996 | Samson et al. | 604/96 |
| 5,640,970 | 6/1997 | Arenas | 128/772 |

*Primary Examiner*—Corrine M. McDermott
*Assistant Examiner*—Cris L. Rodriguez
*Attorney, Agent, or Firm*—Merchant, Gould, Smith, Edell, Welter, & Schmidt, P.A.

[57] ABSTRACT

An infusion guide wire of superelastic nickel titanium is disclosed comprising a lumen extending longitudinally through the wire and a distal portion with a smaller outer diameter than a proximal portion. One or more intermediate portions of intermediate outer diameters can be provided, as well. An occlusion balloon can be attached to the distal portion, and inflated through the lumen. Alternatively, or in conjunction with the occlusion balloon, drugs or other agents can be delivered through the lumen.

3 Claims, 4 Drawing Sheets

NICKEL TITANIUM GUIDE WIRES FOR OCCLUSION AND DRUG DELIVERY

This application claims the benefit of U.S. Provisional application Ser. No. 60/004,349, filed on Sep. 27, 1995, now abandoned.

FIELD OF THE INVENTION

The present invention relates to guide wires and, more particularly, a guide wire of superelastic nickel titanium which comprises a lumen for the infusion of a fluid. The guide wire can also comprise an occlusion balloon, which can be inflated by infusion of fluid through the lumen. Alternatively, or in conjunction with occlusion, drugs or other agents can be delivered to a desired site through the lumen.

BACKGROUND OF THE INVENTION

Guide wires are commonly used in medical procedures to assist in the advance and proper positioning of diagnostic and therapeutic devices in lumens, vessels or cavities of the body. Having a smaller outer diameter and greater flexibility, pushability and torqueability than typical diagnostic or therapeutic devices, the guide wire is easier to advance to the desired site. For example, in percutaneous transluminal coronary angioplasty (PTCA) and percutaneous transluminal angioplasty (PTA), a guide wire is typically first inserted into and advanced through the vessels of the cardiovascular system, through a stenosis. The progress of the guide wire can be monitored on a fluoroscope. When the guide wire is properly positioned, a guide catheter is advanced over the guide wire, proximate the site. Then, a dilatation catheter is advanced over the guide wire, through the guide catheter, into the stenosis. A drug infusion catheter may be advanced to the site of a PTCA or PTA procedure over the guide wire, as well. For coronary applications, the diameters of typical guide wires are between about 0.010-0.018 inches. Dilatation and drug infusion catheters are advanced to thrombi over guide wires throughout the cardiovascular system, as well.

Guide wires can assist in the proper positioning of devices in other parts of the body, such as the urethra, bladder, prostate, rectum, bile duct, pancreatic duct and central nervous system, such as along the spinal column, as well.

The guide wire is typically a thin wire of stainless steel, for example. Guide wires are also made of a inner core of stainless steel with a soft coil of platinum or tungsten, for example, soldered or otherwise attached to its distal tip. The guide wire may be coated with Teflon®. The distal end of the coil is typically melted to form a semi-hemispherical shape, which enables atraumatic passage of the wire through a vessel. The wire core can have a constant diameter or a constant taper toward the distal end. A coil may be provided over the entire length of the wire core for improved flexibility and control, as well.

Guide wires are also made of superelastic nickel titanium, which has a modulus of elasticity which is about two-thirds of that of steel. The superelastic nickel titanium guide wires are less likely to kink during advancement through the turns of the cardiovascular system than steel. A superelastic nickel titanium guide wire is disclosed in U.S. Pat. No. 5,411,476, for example.

Infusion guide wires are also available which provide a central lumen for conveying drugs or other agents or contrast media through the guide wire for delivery proximate the distal end. Such infusion guide wires typically comprise a tightly wound coil of stainless steel defining a lumen. The coil is covered by a flexible sheath. An outer coil of stainless steel wound in an opposite pitch as the inner coil can be provided over the sheath for improved control. Proximal portions of the coil or coils are separated to enable the entry of fluid into the lumen. Distal portions are separated to enable the exit of the fluid. A solid core wire with tapered sections can be provided within the lumen to further improve control of the wire. Such infusion catheters typically have an outer diameter of 0.022-0.038 inches. Guide wires of this type are described in U.S. Pat. Nos. 5,376,083, 5,373,619 and 5,154,705, for example, and are available from Lake Region Manufacturing Company, Inc., for example.

Dilatation guide wires are also known wherein a dilatation balloon of polyethylene, polyethylene terephthalate, nylon or polyurethane, for example, is attached to the distal portion of a guide wire through which inflation fluid can be infused. Examples of such "fixed wire balloon catheters" include the Probe from Bard and the Ace from Scimed.

For certain applications, such as in the cerebral arteries, which can have diameters of approximately 2 mm, the guide wires with infusion lumens for inflation of occlusion balloons or drug delivery are too large to reach the desired site. In addition, the guide wire lumens of dilatation catheters, infusion catheters and guide catheters must be large enough to accommodate the guide wire, as well as other devices which may be advanced over it. Smaller guide wires allow for smaller guide wire lumens in these other devices, or the accommodation of other devices or functions through those lumens.

SUMMARY OF THE INVENTION

In accordance with one embodiment of the invention, a guide wire comprising a nickel titanium wire is disclosed comprising a distal portion and a proximal portion, wherein the distal portion has a smaller outer diameter than the proximal portion. A lumen extends longitudinally through the wire.

In accordance with another embodiment of the invention, an occlusion guide wire is disclosed comprising a superelastic nickel titanium wire comprising a distal portion and a proximal portion, wherein the distal portion has a smaller outer diameter than the proximal portion. A lumen extends longitudinally through the wire. A distal end of the lumen is sealed. An occlusion balloon is coupled to the distal portion, in fluid communication with the lumen. Drug delivery ports are optionally provided in the distal portion proximal or distal to the occlusion balloon.

DETAILED DESCRIPTION OF THE INVENTION

Figure 1:
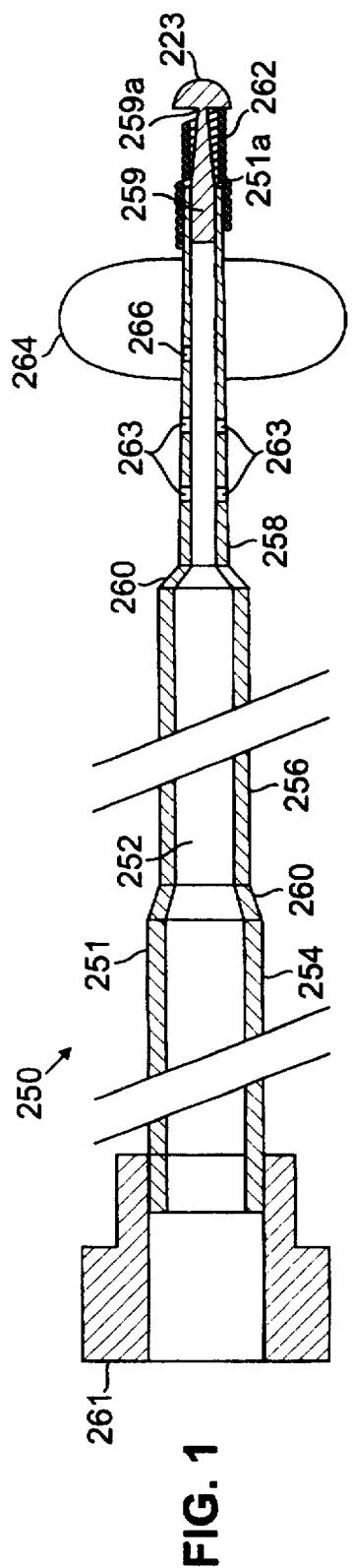
FIG. 1 is a cross sectional view of a guide wire with an occlusion balloon and optional drug delivery ports proximal to the balloon in accordance with one embodiment of the present invention.

FIG. 1 is a cross sectional view of a guide wire 250 in accordance with the present invention. The guide wire 250 comprises a hollow wire 251 of superelastic nickel-titanium with a central lumen 252. The proximal portion of the guide wire 250 must have sufficient rigidity for forces exerted on the proximal end, such as a forward force to advance the wire or a rotational force to turn the wire, to be sufficiently translated to the distal portion. The intermediate and distal portion of the guide wire 250, however, must also be soft enough to follow the turns of the vasculature and not damage tissue. Decreasing the outer diameter of a portion of the wire 251 decreases its rigidity. The wire 251, therefore, comprises at least two and preferably three sections 254, 256, 258, wherein the proximal portion 254 has a greater outer diameter than the intermediate portion 256, which has a greater outer diameter than the distal portion 258. Additional sections can be provided, as well.

In the embodiment of FIG. 1, the guide wire 250 comprises a proximal portion 254, which preferably has an outer diameter of about 0.018 inches, an intermediate portion 256, which preferably has an outer diameter of about 0.015 inches and a distal portion 258, which preferably has an outer diameter of about 0.012 inches. Tapered sections 260 separate each portion. The inner diameter of the proximal portion 254 is about 0.015 inches, the inner diameter of the intermediate portion 256 is about 0.012 inches and the inner diameter of the distal portion 258 is about 0.009 inches. In a guide wire with a length of about 180 cm, for example, the proximal portion 254 of the wire 250 can have a length of about 110 cm, the intermediate portion 256 can have a length of about 54.5 cm and the distal portion 258 can have a length of about 15.5 cm.

A solid rod or core 259 of stainless steel or tungsten, for example, is inserted into the lumen 252 of the distal portion 258 to seal the distal end of the wire 250. It can be soldered or adhered in place. Stainless steel grades 304 or 306 may be used, for example. The rod 259 preferably extends out of the lumen 252, beyond the distal end 251a of the wire 251.

The portion of the rod 259 extending from the lumen 252, is preferably tapered towards its distal end to increase its flexibility. The portion of the rod 259 within the lumen 252 can have a diameter of about 0.008 inches, which can decrease to about 0.003 inches at its distal end 259a, for example. A semi-hemispherical weld 223 is preferably formed at the distal end 259a of the rod 259 by melting the tip of the rod 259 back in a plasma weld, for example, to protect tissue during advancement of the guide wire 250.

A wire coil 262 of tungsten or platinum, for example, is also preferably attached to the distal portion 258 and to part of the rod 259, to soften the distal tip of the guide wire 250 to protect tissue. In addition, the tungsten or platinum coil is radiopaque, enabling tracking of the distal tip of the guide wire on a fluoroscope. The coil can be soldered or attached to the distal portion 250 by an adhesive. The coil 262 preferably extends about 2-3 cm from the tip 251a of the distal portion 258. The rod 259 preferably extends out of the lumen 252 of the distal portion 258, to support the coil. A doctor can bend the coil 262 and rod 259 prior to a procedure, to ease the advance of the guide wire 250 to the desired site. Alternatively, the distal portion 258 of the guide wire 250 may be heat treated to remove its superelastic, shape memory properties, as is known in the art, so that a doctor can bend the distal portion 258 of the guide wire 250.

In this embodiment, an occlusion balloon 264 is coupled to the distal portion 258 of the guide wire 250. A port 266 is provided through the wall of the distal portion 258, to provide fluid communication between the central lumen 252 and the region encompassed by the occlusion balloon 264. The occlusion balloon 264 can be any soft, non-thrombogenic material known in the art, such as polyamide, polyamide copolymer, polyethylene, PEBAX®, nylon, Kraton®, silicone, and C-Flex®, which is a blend of polyurethane and silicone available from Polymer Technologies, Inc., Fla., for example. The occlusion balloon 264 can be attached to the guide wire 250 by an adhesive. Cyanoacrylic adhesives, ultraviolet activated adhesives or epoxies may be used, for example. Preferably, the balloon inflation port 266 has a diameter of at least about 0.005 inches. Inflation fluid can be provided to the lumen 252 through a suitable connector 261, as is known in the art.

Drugs or other agents can also be delivered through the guide wire 250 by providing optional small ports 263, shown in FIG. 1, proximal to the occlusion balloon 264. The drug can inflate the balloon and then seep out of the ports 263. The delivery ports 263 preferably have a diameter of about 0.001–0.004 inches. Drugs or other agents can also be infused into the lumen 252 through the connector 261.

Figure 11:
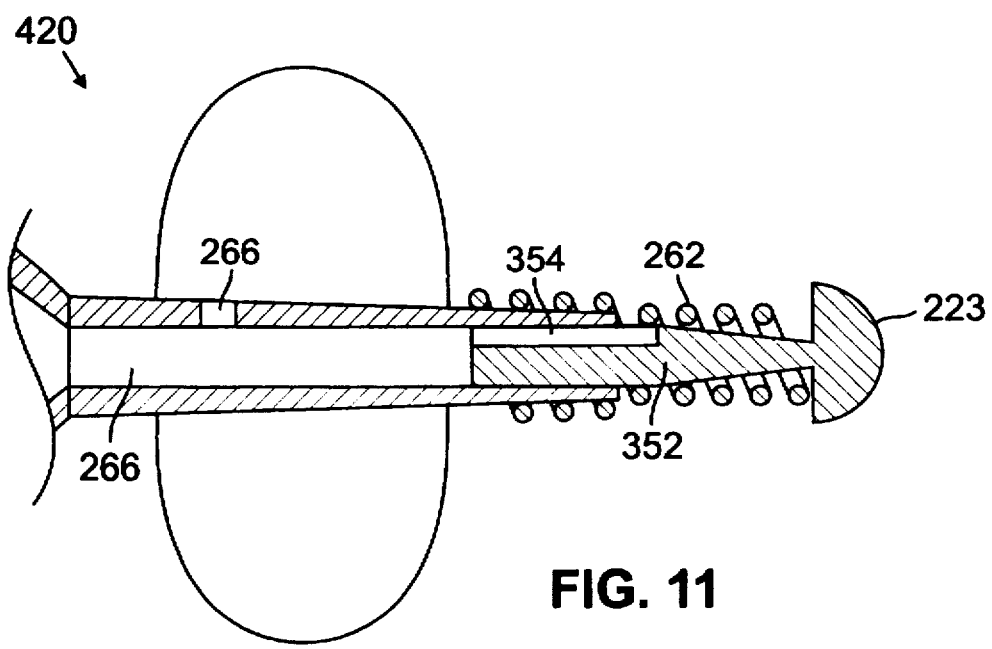
FIG. 11 is a cross sectional view of an occlusion guide wire in accordance with another embodiment of the present invention, wherein the drug or other agent is delivered distal to the occlusion balloon.

The guide wire 250 of FIG. 1 can be used to deliver drugs or agents to the site of a PTCA or PTA procedure to prevent restenosis, for example, where the blood flow in the vessel is towards the distal end of the guide wire 250. The occlusion balloon 264 then maintains the drug in the proximity of the site. The guide wire 250 could also be used to deliver lytic agents into or proximate a thrombus. The occlusion balloon 264 then prevents the passage of thrombolytic material beyond the balloon, through the cardiovascular system. Examples of appropriate drugs or agents are listed below. The ports 263 can also be provided in the distal portion of the wire 258, distal to the occlusion balloon, as shown in FIG. 11.

Figure 2:
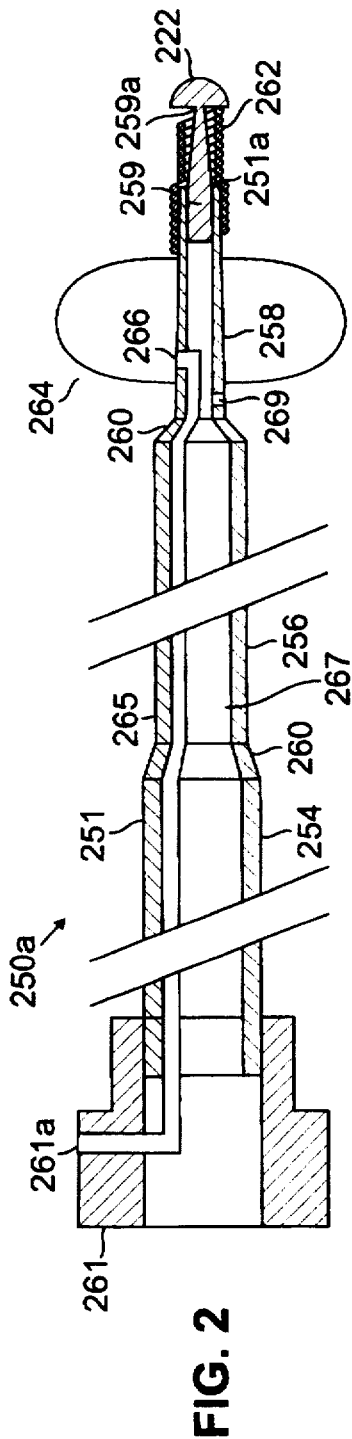
FIG. 2 is a cross sectional view of a guide wire with an occlusion balloon and optional drug delivery ports proximal to the balloon in accordance with another embodiment of the present invention.

FIG. 2 is an alternative embodiment of the guide wire 250, wherein inflation fluid can be provided to the occlusion balloon through a plastic tube attached to the wall of the lumen 252. A port 261a can be provided in the connector 261 to provide the inflation fluid. The tube can be adhered in place within the lumen 252. This embodiment can also be used to deliver drugs or other agents, such as lytic agents, through the lumen 252, through the optional ports 269.

Figure 3:
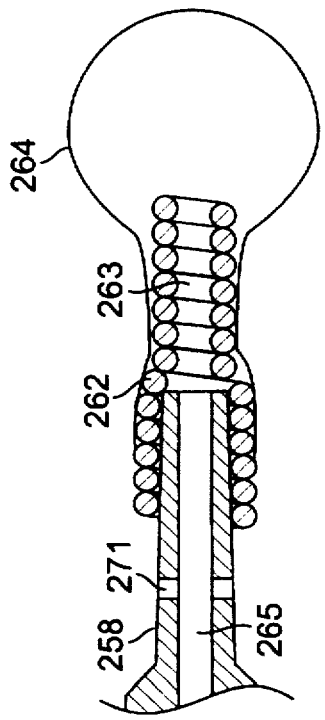
FIG. 3 is a cross sectional view of the distal portion of a guide wire with an occlusion balloon attached over the distal end of the guide wire and optional drug delivery ports in accordance with another embodiment of the present invention.

The occlusion balloon 264 can also be attached to the distal tip of the guide wire 200, over the coil 262, as shown in FIG. 3. The coil 262 defines a hollow center 263, which provides fluid communication between the central lumen 265 of the wire 250 and the balloon 264. The occlusion balloon 264 can also be attached to the coil 262 by an adhesive. This embodiment can also be used for the delivery of drugs or other agents by providing small ports 271 through the wall of the distal portion 258, proximal to the occlusion balloon 264. As discussed above, the drug or agent can both inflate the balloon through the central lumen 252 and, when the balloon is inflated, seep out of the ports 271.

Figure 4:
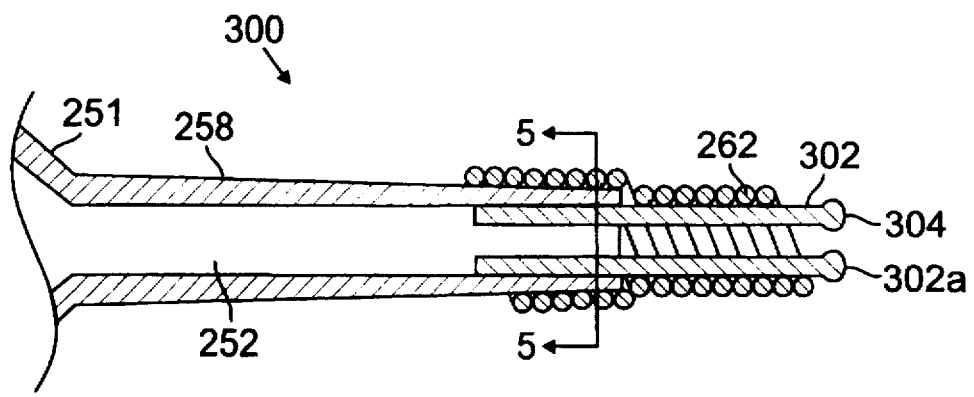
FIG. 4 is a cross sectional view of the distal portion of a guide wire which delivers drugs or other agents through its distal tip in accordance with another embodiment of the present invention.
Figure 5:
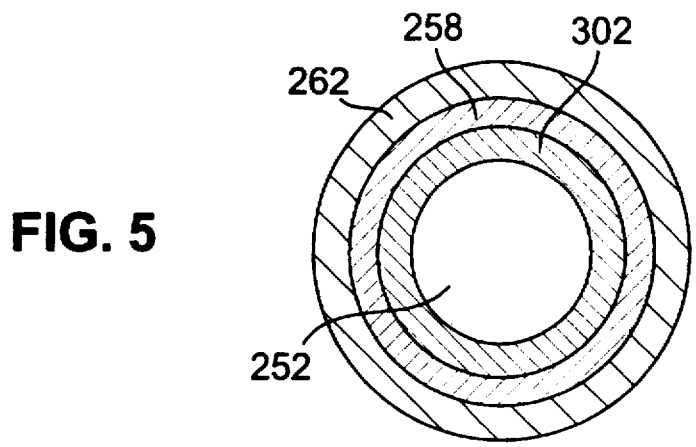
FIG. 5 is a cross sectional view of the guide wire of FIG. 4 through line 5—5 in FIG. 4.

FIG. 4 is a cross-sectional view of a drug delivery guide wire 300 in accordance with a preferred embodiment of the present invention. The guide wire 300 comprises a hypo-tube 302 of steel extending out of the distal portion 258 of the nickel titanium wire 251. The coil 262 is attached to the outside surface of the distal portion 258 and the hypo-tube 302. As above, a doctor can bend the hypo-tube 302 to put a desired angle on the tip of the guide wire 300 to ease advancement of the guide wire 300 to a desired site. The distal tip of the tube 302 is preferably melted to form a rounded, bulbous portion 302a, to protect the vessel walls. Alternatively or in addition to the bulbous portion 302a, a polymeric covering or coating of a soft material such as PEBAX® or polyurethane may also be added over the tip 302a to protect vessel walls. Drugs or other agents can be delivered through the lumen 252 and hypo-tube 302, out the distal opening 304 of the tube 302. The guide wire 300 can be used to deliver lytic agents directly towards a thrombus, for example. The distal tip of the guide wire 300 can also be inserted into the thrombus for drug delivery within the thrombus. FIG. 5 is a cross-sectional view of the guide wire 300 through line 5—5 of FIG. 4. Appropriate hypo-tubes are available from Vita-Needle Co., Needham, Mass., for example.

Figure 6:
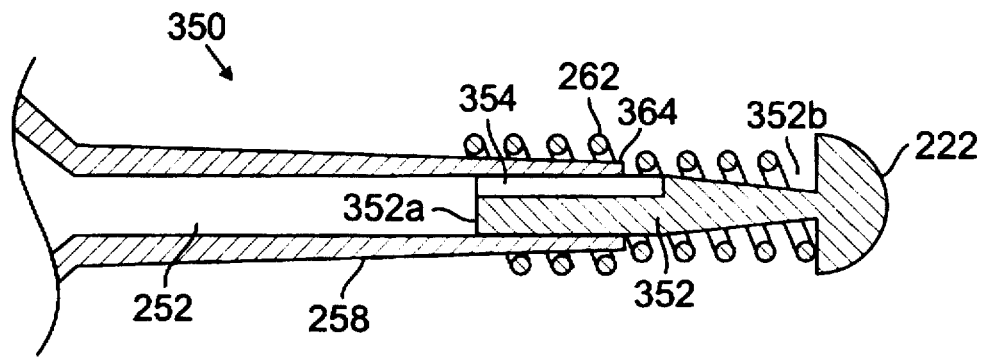
FIG. 6 is a cross sectional view of the distal portion of a drug delivery guide wire in accordance with another embodiment of the present invention, wherein drugs or other agents can be delivered through a coil at the distal end of the guide wire.
Figure 7:
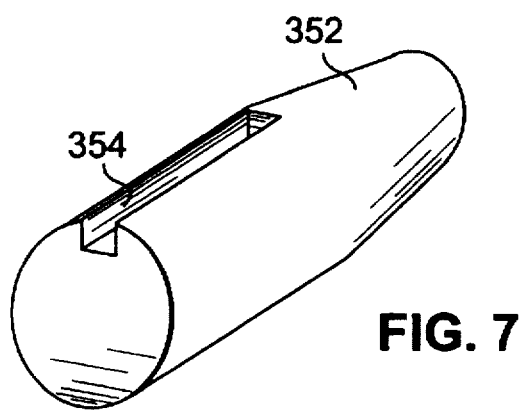
FIG. 7 is a perspective view of a tube placed in the distal portion of the guide wire of FIG. 6.
Figure 8:
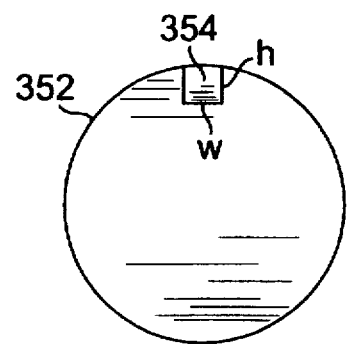
FIG. 8 is a front view of the tube of FIG. 7.

FIG. 6 is a cross sectional view of a guide wire 350 in accordance with another embodiment of the invention, wherein drug is delivered through the coil 262. The coil 262 is loosely wound to provide space between adjacent turns so that the drug can pass. A solid rod 352 of steel or tungsten, for example, extends from the distal portion 258 of the wire, as in FIG. 1. The rod 352 includes one or more grooves 354 extending from its proximal end 352a partially towards the distal end 352b. The groove 354 terminates beyond the distal tip 364 of the distal portion 258 of the wire, within the coil 262. FIG. 7 is a perspective view of the rod 352, showing the groove 354. FIG. 8 is a front view of the rod 352 and groove 354. The groove 354 provides fluid communication between the lumen 252 and the exterior of the guide wire 350 through the coil 262. The rod can be soldered, glued or otherwise attached within the distal portion of the wire. The groove can be a height "h" of about 0.0035 inches, a width "w" of about 0.0035 inches, as shown in FIG. 8, and any desired length such that the groove terminates within the coil 262. The guide wire 350 of this embodiment can be used to deliver drugs or other agents within a thrombus, proximate a thrombus or into a region of a lumen, vessel or cavity. The portion of the rod 352 distal to the end of the groove is preferably tapered, as discussed above.

Figure 9:
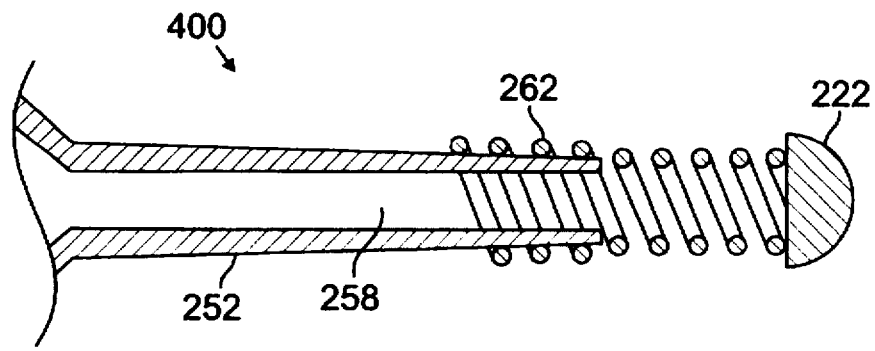
FIG. 9 is a cross sectional view of a distal portion of another embodiment of the invention, wherein a drug or other agent can be infused through the coil at the distal end of the guide wire.

FIG. 9 is a cross-sectional view of a drug delivery guide wire 400, wherein drugs or other agents are delivered directly from the lumen 252, through a loosely wound coil 262. The coil 262 is attached to and extends beyond the distal portion 258 of the wire. In this embodiment, a semi-hemispherical weld 225 is formed out of the distal end of the coil 262, as is known in the art.

Figure 10:
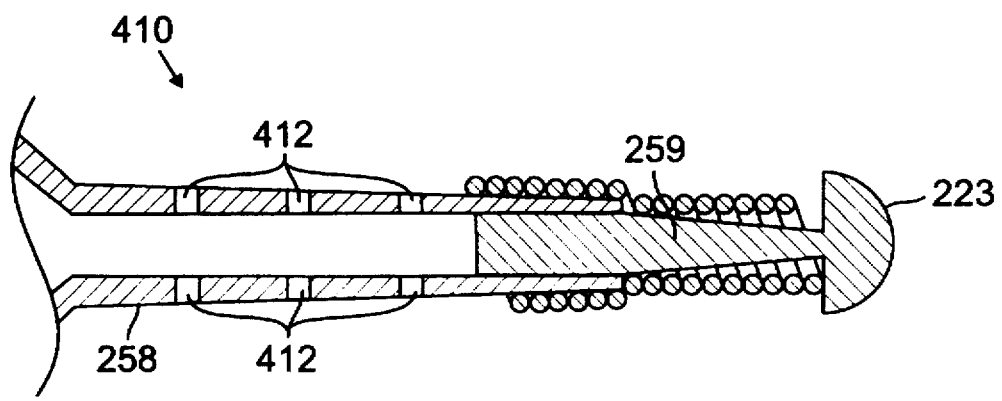
FIG. 10 is a cross sectional view of an infusion guide wire in accordance with another embodiment of the invention, wherein the drug or other agent is delivered through the walls of the wire.

FIG. 10 is a cross-sectional view of an alternative drug delivery guide wire 410, wherein the distal portion 258 is sealed by a solid rod 259, as in FIG. 1. A plurality of drug delivery ports 412 are provided through the distal portion 258.

FIG. 11 is a cross-sectional view of another embodiment of the present invention wherein a drug delivery guide wire 420 has an occlusion balloon proximal to the point of drug delivery. The same rod 352 with the groove 354, as in the embodiment of FIG. 6, can be provided at the distal tip of the nickel titanium wire. A port 266, as in FIG. 1, provides fluid communication between the lumen 252 and the region encompassed by the balloon 264. The drug inflates the occlusion balloon 264 and exits the lumen 266 through the loosely wound coil 262. This embodiment may be used for drug delivery wherein the blood flow is toward the proximal portion of the guide catheter.

The superelastic nickel titanium wire is preferably about 50% nickel, 50% titanium. A composition of about 50.8% nickel, and the remainder titanium, may be used, for example. Other elements, such as iron, cobalt, vanadium and copper, for example, may also be included, as is known in the art. The wire should be superelastic at room temperature.

The guide wire 250 of superelastic nickel titanium with decreasing outer diameters may be manufactured in a metal drawing process including cold drawing and heat treating. Suitably shaped wire appropriate for cardiovascular and other such applications is available from Nitinol Devices and Components, Inc., Freemont, Calif., and Euroflex, Germany. The wire can also be ground to the desired outer diameters by a centerless grinder, for example, as is known in the art.

The guide wires of the present invention can be used in any application where conventional guide wires would be used. They are particularly advantageous where drug delivery or occlusion is required in narrow vessels or lumens. For example, the guide wires of the present invention are particularly suitable for use in the cerebral arteries. The guide wires of the present invention can be used to occlude the region distal to a cerebral thrombus or site of a cerebral angioplasty procedure, for example, to prevent the escape of thrombolytic material or plaque. Both sides of a thrombus or site can be occluded by the use of two such guide wires. The guide wires of the present invention can also be used to deliver drugs or other agents, such as lytic agents, into or proximate a cerebral thrombus or to deliver drugs, such as anticoagulants or antiproliferatives, to the region of a cerebral vessel to prevent restenosis. Guide wires with reduced outer diameters in accordance with the present invention also enable the use of diagnostic or therapeutic catheters, such as dilatation catheters, with guide wire lumens of reduced diameters and hence catheters with reduced outer diameters.

The guide wire of the present invention can also be used to treat deep vein thrombosis, as described and claimed in "Systems and Methods for Drug Delivery including Treating Thrombosis By Driving A Drug or Lytic Agent Through The Thrombus By Pressure", U.S. Ser. No. 08/534,856, filed on Sep. 27, 1995, assigned to the assignee of the present invention As described in that application, the guide wire of the present invention can be used to occlude a region distal to a thrombus and optionally to deliver drugs or other agents such as lytic agents, under pressure, into the distal region. In that system, a guide catheter including an occlusion balloon occludes the region proximal to the thrombus. The guide catheter comprises a lumen for providing inflation fluid to the occlusion balloon and a lumen for accommodating the guide wire and infusion catheter. Material, such as thrombolytic material and the delivered drug or agent, can be evacuated from the proximal region through the guide wire/infusion catheter lumen. The evacuated material may be filtered and the drugs or lytic agent redelivered into the distal region.

Drugs or agents which can be delivered through the guide wires of the present invention include anticoagulants and antiproliferatives to prevent restenosis after PTCA or PTA procedures. Anticoagulants include heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FIX, FVIII, FV, FVIIa and tissue factor, for example. Antiproliferatives include dexamethasone, growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, bifunctional molecules comprising an antibody and a cytotoxin. Polaxymer 188, another antiproliferative, can also be delivered through the guide wires of the present invention to pave or line the walls of an artery to prevent smooth muscle growth.

Vasodilators, such as nitroglycerin, nitroprusside or other nitric oxide liberators, can also be delivered. The vasodilator can also include other suitable vasoactive agents such as beta receptor blocking drugs, inhibitors of intra-cellular calcium transport, prostaglandins, thromboxane antagonists, and the like.

Other drugs or agents which can be delivered include substances which inhibit platelet deposition and thrombus formation or lytic agents which promote thrombolysis and thrombus dissolution, such as plasmin, tissue plasminogen activator (tPA), recombinant tissue plasminogen activator (rTPA), urokinase, single chain prourokinase (scuPA), streptokinase, prostaglandins, cyclooxygenase inhibitors, phosphodiesterase inhibitors, thromboxane synthetase inhibitors, antagonists of glycoprotein receptors including (GP) Ib, GP IIb/IIIa, antagonists of collagen receptors, and antagonists of platelet thrombin receptors, for example.

Drugs or agents which directly affect platelet metabolic function can also be delivered. Examples of such substances include prostaglandins, cyclooxygenase inhibitors, phosphodiesterase or thromboxane synthetase inhibitors, inhibitors of calcium transport, or elevators of cyclic adenosine monophosphate (cyclic AMP).

The guide wires of the present invention can be used in any lumen, vessel or cavity of the body.

The above embodiments are examples of systems and methods of the present invention, which are defined in the following claims.

I claim:

1. A guide wire comprising:

a nickel titanium wire comprising a distal portion and a proximal portion, wherein the distal portion has a smaller outer diameter than the proximal portion, at least one intermediate portion between the distal and proximal portions, the intermediate portion having an outer diameter less than the outer diameter of the proximal portion and greater than the outer diameter of the distal portion, and a lumen extending longitudinally through the wire, the lumen having a distal portion that is sealed by a solid tube; and an occlusion balloon attached to the distal portion of the wire;

wherein the distal portion of the wire defines at least one port providing fluid communication between the lumen and the balloon, and at least one port proximal to the occlusion balloon providing fluid communication between the lumen and the exterior of the guide wire.

2. An occlusion guide wire comprising:

a superelastic nickel titanium wire comprising a distal portion and a proximal portion, wherein the distal portion has a smaller outer diameter than the proximal portion, and a lumen extending longitudinally through the wire and having a distal end, the distal end of the lumen being sealed; and an occlusion balloon coupled to the distal portion of the wire, in fluid communication with the lumen;

wherein the distal portion of the wire defines at least one port providing fluid communication between the lumen and the balloon and defines at least one additional port proximal to the balloon.

3. The guide wire of claim 2, further comrising a coil, wherein a portion of the coil is attached to the distal portion of the wire and a portion of the coil extends beyond the distal portion of the wire.

* * * * *